United States Patent

Snyder

(10) Patent No.: US 8,128,816 B2
(45) Date of Patent: Mar. 6, 2012

(54) PISTON MOVEMENT CONTROL FOR PREPARATIVE CHROMATOGRAPHY COLUMN

(75) Inventor: Mark A. Snyder, Oakland, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 64 days.

(21) Appl. No.: 12/813,844

(22) Filed: Jun. 11, 2010

(65) Prior Publication Data

US 2011/0139718 A1 Jun. 16, 2011

Related U.S. Application Data

(60) Provisional application No. 61/218,767, filed on Jun. 19, 2009.

(51) Int. Cl.
*B01D 15/08* (2006.01)
(52) U.S. Cl. ..................... 210/198.2; 210/656
(58) Field of Classification Search .......... 210/635, 210/656, 659, 198.2; 422/70
See application file for complete search history.

(56) References Cited

U.S. PATENT DOCUMENTS

| 750,449 | A | | 1/1904 | Gillard |
| 3,662,470 | A | | 5/1972 | Sasgen |
| 3,910,765 | A | | 10/1975 | Tinklepaugh et al. |
| 5,169,522 | A | * | 12/1992 | Shalon et al. ............ 210/198.2 |
| 5,645,717 | A | * | 7/1997 | Hjerten et al. ............ 210/198.2 |
| 6,197,198 | B1 | | 3/2001 | Messinger et al. |
| 7,351,334 | B2 | * | 4/2008 | Allington et al. ........ 210/198.2 |
| 2008/0272042 | A1 | | 11/2008 | Hofmann |

* cited by examiner

*Primary Examiner* — Ernest G Therkorn
(74) *Attorney, Agent, or Firm* — Kilpatrick Townsend and Stocton LLP.; M. Henry Heines

(57) ABSTRACT

In an axial-flow preparative chromatography column that contains a piston, commonly termed an adaptor, that is lowered over the top of the resin, the ability to lower the piston in a controlled manner to minimize the chances of damage to the resin is achieved by use of an aperture either in the piston head itself or in a compound bolt that secures the upper column frit to the piston head. The aperture is closed with a removable plug during storage and use of the piston head and column. During packing of the bed, however, the plug is replaced by a graduated rod operating as a dipstick to allow the operator to determine the distance between the bottom face of the piston head and the upper surface of the column packing.

4 Claims, 4 Drawing Sheets

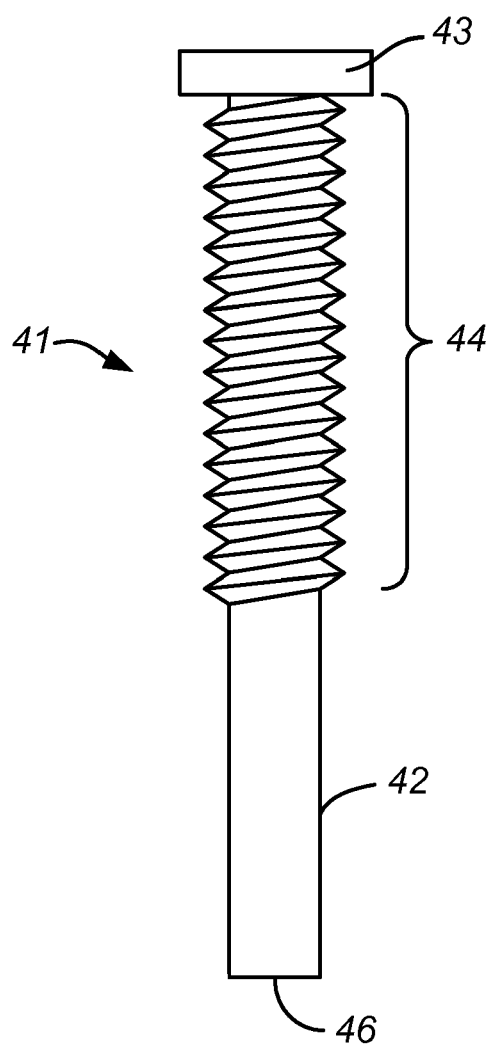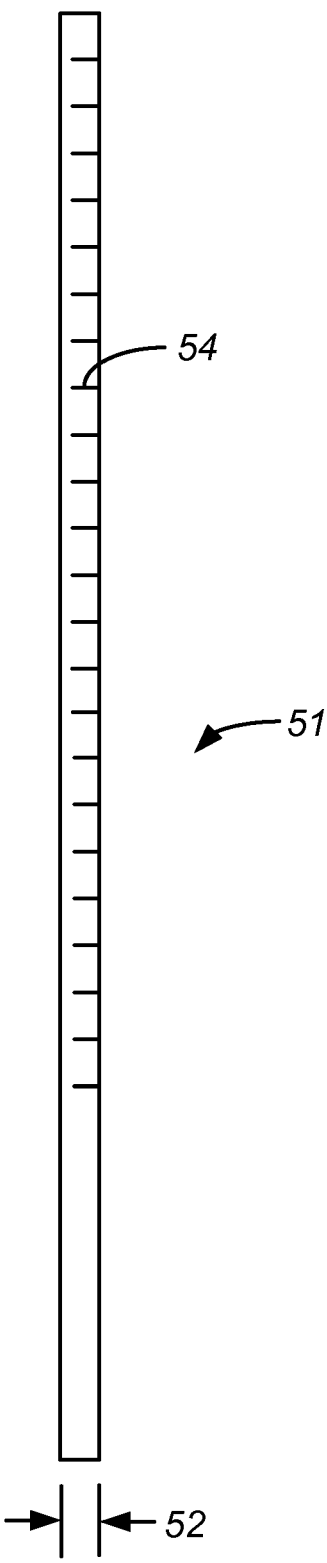
FIG. 3
FIG. 4

PISTON MOVEMENT CONTROL FOR PREPARATIVE CHROMATOGRAPHY COLUMN

CROSS-REFERENCE TO RELATED APPLICATION

This application claims the benefit of U.S. patent application Ser. No. 61/218,767, filed Jun. 19, 2009, the contents of which are incorporated herein by reference.

BACKGROUND OF THE INVENTION

1. Field of the Invention

This invention resides in the field of preparative chromatography columns.

2. Description of the Prior Art

Preparative chromatography is a separation technique used to extract individual chemical species in quantities sufficient for commercial use from mixtures of species. Preparative chromatography thus differs from analytical chromatography whose purpose is to detect the presence or concentration of particular components in the mixture or to determine the composition of the mixture as a whole. Preparative chromatography is commonly performed by passing a relatively large quantity of a liquid source mixture through a column packed with a solid resin. Separation of the different species in the mixture and extraction of the species of interest can occur by any of a wide variety of interactions between the source mixture solution, referred to as the mobile phase, and the resin, referred to as the stationary phase. Examples of these interactions are ion-exchange chromatography, affinity chromatography, and liquid-liquid or partition chromatography.

In an axial-flow preparative chromatography column, the axial length of the column must be limited to avoid an excessive pressure drop through the column, since a high pressure drop requires a high pump pressure to force the mobile phase through the column, high power to drive the pump, or both. To extract the separated species in a commercially useful quantity, therefore, a column of relatively large diameter is needed. The typical preparative chromatography column is thus at least several centimeters in diameter, and in some cases, columns with diameters of a meter or more are used. Columns of large diameters present certain challenges, however, notably the difficulty in distributing the flow of mobile phase across the width of the column, as one needs to do to achieve efficient separation and a high resolving power. Flow distributors are typically used at both ends of the column to overcome this problem. In some cases as well, particularly in columns that are arranged vertically with downward flow, the solid phase is packed in the column in a manner that eliminates or minimizes void spaces at the inlet side of the packing. Uniform packing can be achieved by applying pressure to the resin particles, but pressure can also cause fracture or pulverization of portions of the packing material, particularly if the material is incompressible such as ceramic hydroxyapatite or fragile such as controlled-pore glass. The pressure can be applied by use of a sliding piston, also referred to as an adaptor, that is positioned above the resin and is lowered until it contacts the resin. The piston that is typically used also contains flow distribution channels to help distribute the mobile phase across the column width. To avoid damage to the resin particles, the movement of the piston must be closely controlled. Caution is also needed for compressible resins, particularly those resins designed to be compressed by a set percentage relative to their uncompressed state. For these resins, the total amount of resin in the column prior to compression must be known.

SUMMARY OF THE INVENTION

The present invention addresses the need for improved control of piston position and movement in a preparatory chromatography column by incorporating an aperture in the piston head, a removable plug, and a rod with graduated markings or similar indicia. During initial packing of the column, resin slurry is introduced into the column and consolidated to a solid, but not compressed, bed. Consolidation is achieved through liquid flow, piston movement or a combination of both. During packing of the column and consolidation of the resin, the aperture is sealed with the plug to prevent fluid from passing from the column interior into the aperture. Once the bed is consolidated or settled, the plug is replaced by the rod. Thus, placed, the rod extends through the aperture to protrude through the piston head, and the length by which the rod protrudes can be read by the graduations on the rod. The rod is thus inserted until it contacts the consolidated or settled resin bed in the column, thereby serving as a dipstick to indicate the distance between the piston head and the resin bed as well as the height of the settled or consolidated bed. For a piston head whose surface facing the resin bed is covered with a frit that is secured to the piston head by way of a bolt, the aperture referenced above can be a passage through the bolt along the bolt axis. The bolt can extend through the full thickness of the piston head or only a portion of the thickness, in which case the piston head itself will contain a further passage extending through the remaining thickness of the piston head. The removable plug in these embodiments can be a filler bolt that fits in the bolt passage, and the graduated rod will extend through the bolt passage when the filler bolt has been removed. The bolt in these embodiments is a compound bolt that includes a hollowed outer bolt and the filler bolt that can be inserted in the hollow interior of the outer bolt for sealing purposes, and can be removed to allow the outer bolt to accommodate the graduated rod. Both the filler bolt (or in generic terms, the plug) and the graduated rod are insertable from the upper side of the piston head, i.e., the side opposite the side facing the packed bed in the column interior, so that both can be inserted and removed with the piston head in place inside the column.

These and other objects, features, and advantages of the invention will be more fully understood from the description that follows.

BRIEF DESCRIPTION OF THE DRAWINGS

FIG. 3 depicts a filler bolt for insertion into the outer portion shown in FIG. 2.

FIG. 4 depicts a graduated rod for insertion into the outer portion shown in FIG. 2 when the filler bolt of FIG. 3 has been removed.

DETAILED DESCRIPTION OF THE INVENTION AND PREFERRED EMBODIMENTS

The figures hereto illustrate an example of a preparative chromatography column and bed height indicator in accordance with the present invention.

Figure 1:
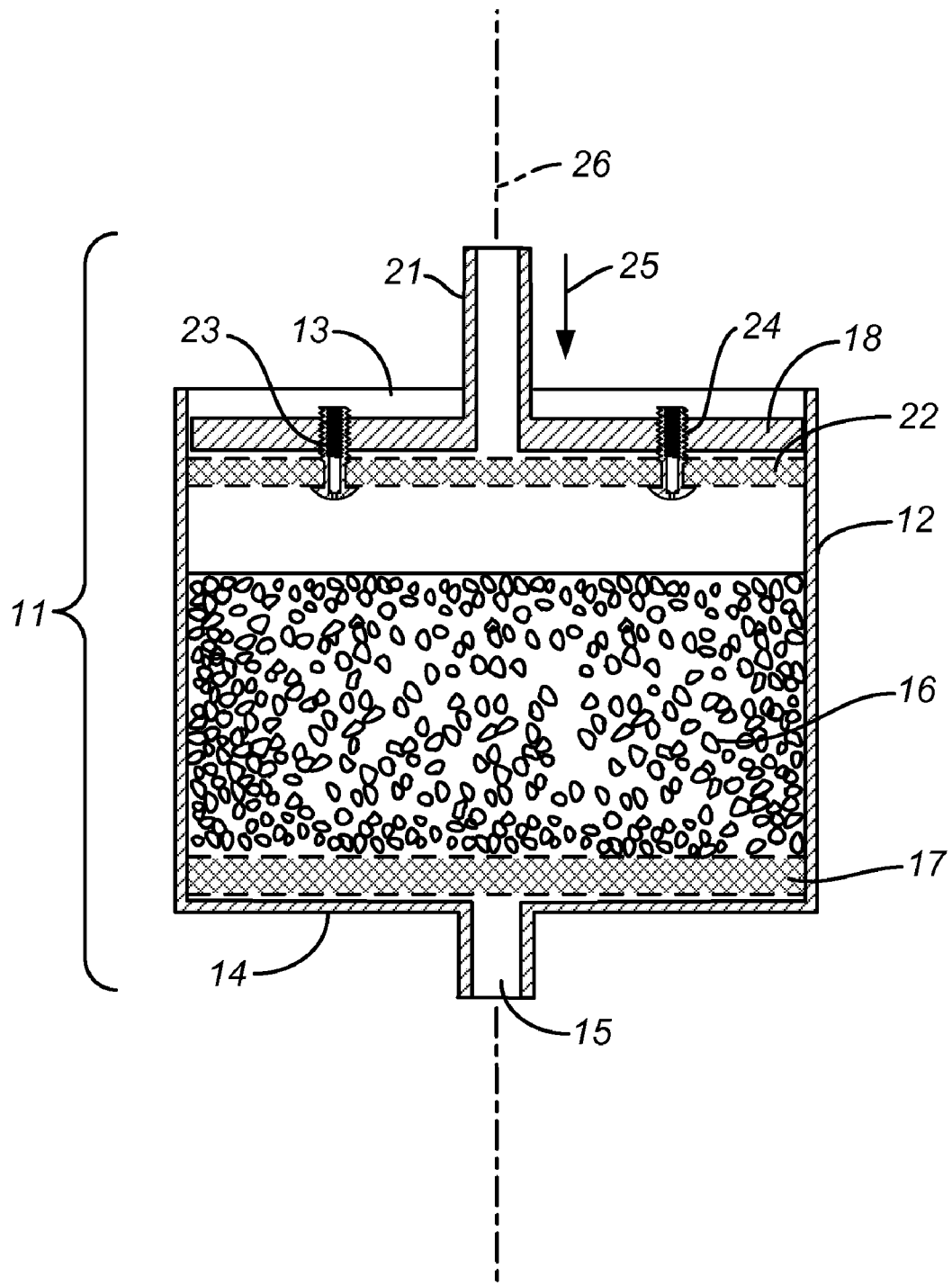
FIG. 1 is a vertical cross section of a preparative chromatography column utilizing features within the scope of the present invention.

FIG. 1 is a vertical cross section of the chromatography column 11. The parts of the column include a cylindrical vessel or tube 12 that is open at the top 13 and closed at the bottom 14 except for an opening 15 at the center of the bottom closure through which the eluent is either drawn from, or allowed to leave, the vessel. The vessel 12 is partially filled with a packed bed 16 of separatory resin, and lining the floor of the column vessel is a frit 17 to support the packed bed 16. Poised above the packed bed is a piston head 18 at the center of which is a feed tube 21 through which the source mixture enters the vessel. Covering the lower surface of the piston head 18 is another frit 22 whose purpose is to help distribute the source mixture entering the column over the width of the column to maximize the use of the packed bed 16. This upper frit 22 is held in place by bolts 23, 24 that pass through the frit and are secured to the piston head 18. The piston head 18 moves downward in the direction of the arrow 25 when packing or compressing the packed bed 16, and this direction is parallel to the longitudinal axis 26 of the piston head. This direction is also the overall direction of the flow through the column.

Figure 2:
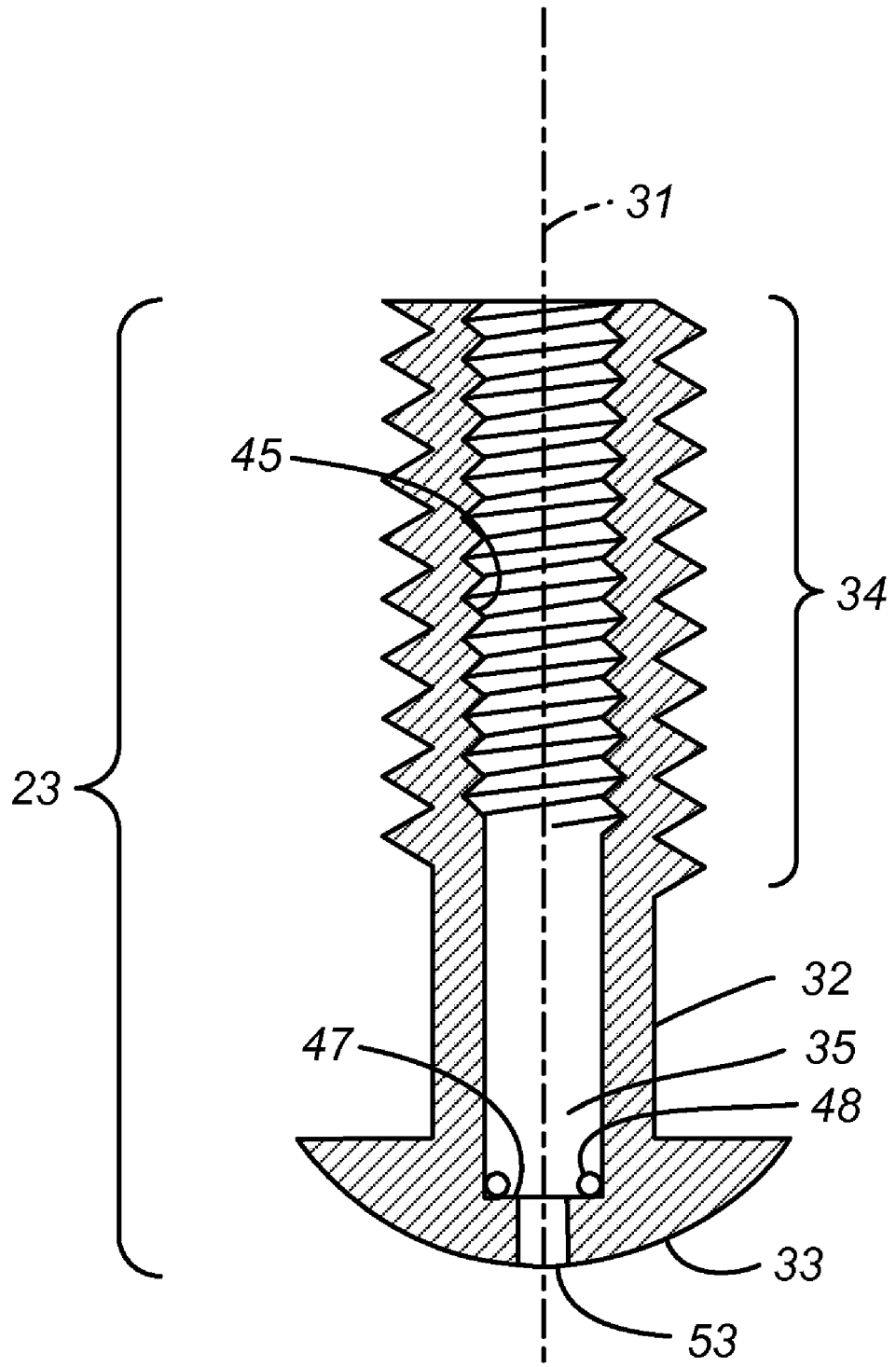
FIG. 2 is a longitudinal cross section of the outer portion of a compound bolt in accordance with the present invention.

An enlarged view of one of the frit-securing bolts 23 is presented in cross section in FIG. 2. The bolt has a longitudinal axis 31, a shaft 32, and an enlarged head 33. The shaft 32 passes through the frit and the piston head (FIG. 1), and the upper portion 34 of the outer surface of the shaft 32 is threaded to mate with threads in a mounting hole in the piston head. The shaft 32 is hollow, forming a passage 35 through the length of the bolt to receive both the plug and the graduated rod, shown in the succeeding figures and discussed below.

FIG. 3 shows the plug, which in this embodiment is a filler bolt 41. The filler bolt has a shaft 42 and an expanded head 43, and a portion 44 of the shaft is threaded to mate with threads 45 on the interior of the bolt passage 35 (FIG. 2). The lower end 46 of the filler bolt in this particular embodiment is flat and abuts an internal shoulder 47 (FIG. 1) in the passage 35 in the frit-securing bolt. An o-ring 48 resting on the shoulder 47 is compressed by the lower end 46 of the filler bolt to serve as a seal. In an alternative arrangement, the shoulder 47 can be replaced with a tapered section and an appropriately shaped gasket or sealing ring can be used in place of the o-ring 48. The expanded head 43 of the filler bolt facilitates the insertion of the filler bolt into the frit-securing bolt 12, as well as its removal.

The filler bolt 41 occupies the passage 35 of the frit-securing bolt during storage and shipping of the piston, and also while the column is being used for chromatographic separations. The graduated rod or dipstick 51, which is shown in FIG. 4, is used during the lowering of the piston head over the packed bed. The diameter 52 of the dipstick 51 is small enough to pass easily through both passages of the frit-securing bolt, i.e., the relatively wide passage 35 (FIG. 2) through which the filler bolt 41 is inserted, and the narrower passage 53 below the shoulder 47. In use, the dipstick is lowered into the combined passage so that the lower extremity of the dipstick protrudes through the head 33 of the frit-securing bolt, until the lower extremity contacts the packed bed. The length of the protruding portion, and hence the distance between the upper frit and the packed bed, is then determined by observing the markings 54 (FIG. 4) on the upper end of the dipstick that are visible above the piston head. The material of construction of the dipstick is chosen to be light enough that it will not penetrate the surface of the packed bed or cause fractures in the packing material upon contact.

Figure 5:
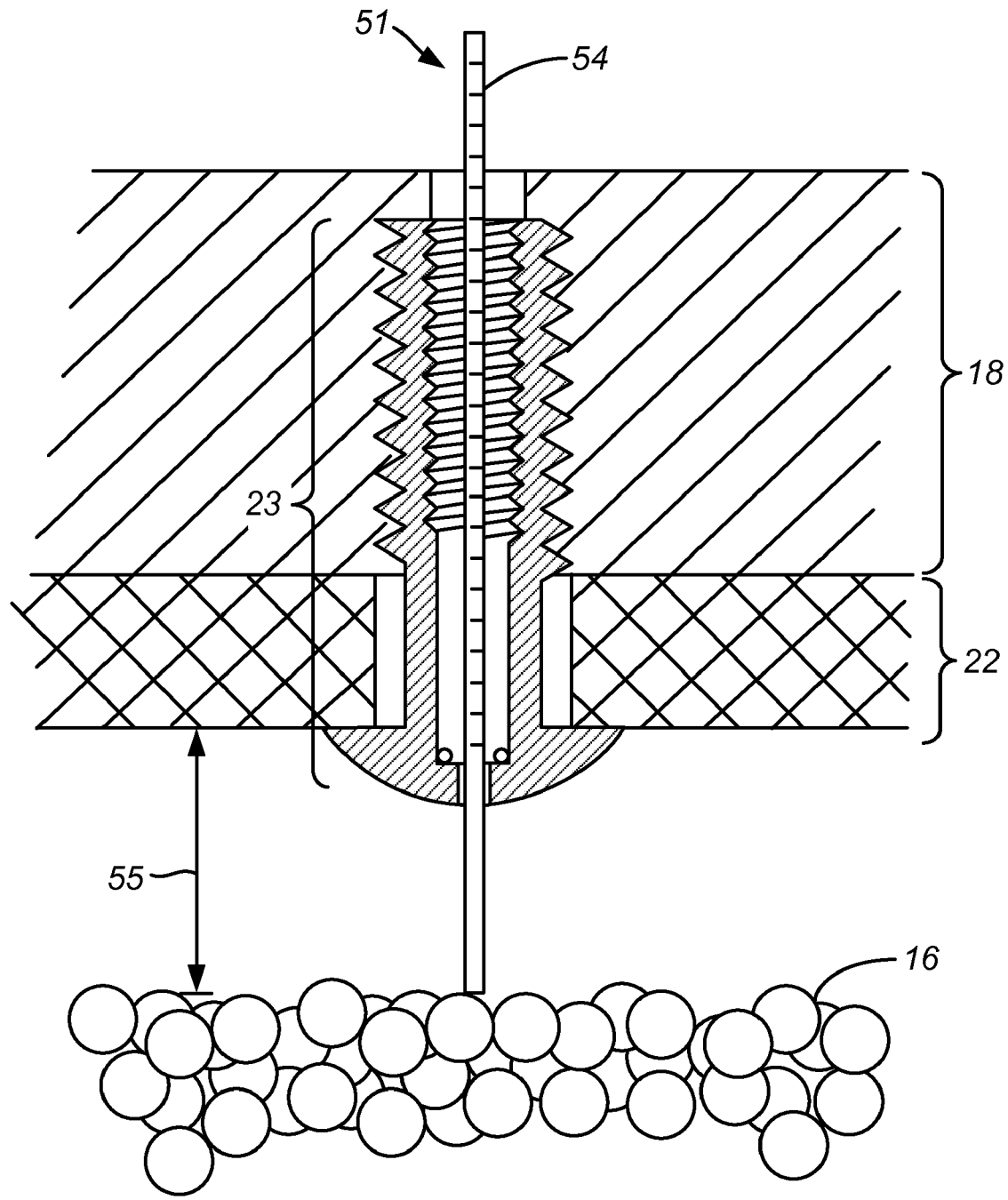
FIG. 5 is a cross section of a piston head and frit on which the invention can be used, with the graduated rod inserted.

FIG. 5 illustrates how the compound bolt might be used. The outer (frit-securing) portion of the compound bolt 23 is shown securing the frit 22 to the piston head 18, and the piston head and frit are raised above the packing material. With the resulting gap between the piston head (with the attached frit) and the consolidated or settled packing material, the filler bolt, which originally occupied the hollow interior of the frit-securing bolt, is removed, and the dipstick 51 is lowered into the hollow frit-securing bolt until the bottom end of the dipstick contacts the packed bed 16. The operator will then observe the exposed graduations 54 on the dipstick to determine the distance 55 between the frit 22 and the consolidated or settled bed 16. The dipstick 51 can then be removed and the filler bolt returned to its original position inside the frit-securing bolt, without moving the piston head, and the piston head can then be lowered by the same distance indicated by the graduations to achieve full contact with the packing material without fracturing the packing material or, in the case of compressible packings, to urge the frit against the packing material to achieve the desired degree of compression.

The terms "a" or "an" as used in the appended claims are intended to mean "one or more." The term "comprise," and variations thereof such as "comprises" and "comprising," when preceding the recitation of a step or an element is intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly stated in this specification of the same word or phrase.

What is claimed is:

1. In a preparative chromatogaphy column comprising a cylindrical tube and a piston head retained within said tube and movable therein along a longitudinal axis, said piston head having an upper surface and a lower surface, the improvement comprising:
    an aperture in said piston head having an axis parallel to said longitudinal axis;
    a removable plug insertable into said aperture from said upper side of said piston head to seal said aperture against fluid entry; and
    a rod insertable through said aperture from said upper side of said piston head when said removable plug is removed therefrom, said rod being sufficiently long to protrude below said piston head to a variable length and bearing indicia to indicate the length of said rod protruding below said piston head.

2. The preparative chromatography column of claim 1 further comprising a frit covering said lower surface of said piston head and a bolt securing said frit to said piston head, said bolt having a bolt axis parallel to said longitudinal axis, and wherein:
    said aperture is formed by a passage through said bolt along said bolt axis; and
    said removable plug means and said rod are insertable in said bolt passage from said upper side of said piston head.

3. The preparative chromatography column of claim 2 wherein said removable plug is a filler bolt insertable in said bolt passage, said filler bolt having external threads mating with internal threads in said bolt passage.

4. The preparative chromatography column of claim 3 wherein said bolt passage contains an internal shoulder sized to abut an end of said filler bolt, and a gasket on said internal shoulder.

* * * * *